United States Patent
Crawford et al.

(10) Patent No.: US 11,424,034 B2
(45) Date of Patent: Aug. 23, 2022

(54) SYSTEMS AND METHODS FOR PREDICTING ANIMAL HEALTH

(71) Applicant: International Business Machines Corporation, Armonk, NY (US)

(72) Inventors: Vanadis M. Crawford, Raleigh, NC (US); Eliza Salkeld, Raleigh, NC (US); Kai K. Arrowood, Raleigh, NC (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 533 days.

(21) Appl. No.: 16/670,263

(22) Filed: Oct. 31, 2019

(65) Prior Publication Data

US 2021/0134459 A1    May 6, 2021

(51) Int. Cl.
| | |
|---|---|
| *G06F 15/18* | (2006.01) |
| *G16H 50/20* | (2018.01) |
| *G06N 3/04* | (2006.01) |
| *G06N 3/08* | (2006.01) |

(52) U.S. Cl.
CPC ........... *G16H 50/20* (2018.01); *G06N 3/0454* (2013.01); *G06N 3/08* (2013.01)

(58) Field of Classification Search
CPC ...... G16H 50/20; G16H 50/30; G06N 3/0454; G06N 3/08; G06N 3/088; G06N 5/003; G06N 20/20
See application file for complete search history.

(56) References Cited

U.S. PATENT DOCUMENTS

| | | | |
|---|---|---|---|
| 10,628,756 B1 * | 4/2020 | Kuper | A01K 5/02 |
| 2016/0037755 A1 | 2/2016 | Webster et al. | |
| 2016/0135431 A1 | 5/2016 | Sheldon et al. | |
| 2017/0223931 A1 * | 8/2017 | Schab | G08B 21/182 |
| 2017/0223947 A1 | 8/2017 | Gall et al. | |
| 2020/0159720 A1 * | 5/2020 | Leong | H04L 63/101 |

FOREIGN PATENT DOCUMENTS

| | | | | |
|---|---|---|---|---|
| CN | 104936439 B | * | 2/2019 | A01J 5/007 |

OTHER PUBLICATIONS

Google Scholar Search Notes.*
Fabiana H.G. Farias, "The Practical Use of Genome Sequencing Data in the Management of a Feline Colony Pedigree," Jul. 27, 2017, pp. 1, 2, 4, 6, 7, 8, Bmc Veterinary Research.

* cited by examiner

*Primary Examiner* — Xin Jia
(74) *Attorney, Agent, or Firm* — Troutman Pepper Hamilton Sanders LLP

(57) ABSTRACT

Embodiments provide systems and methods for predicting animal health of future generations of animals. Historical health and environmental data are collected and analyzed using machine learning to predict animal health of future generations and to understand which factors of health and environmental data affect animal health. Analysis also provides other insights relative to the field of animal husbandry such as anomaly detection.

20 Claims, 5 Drawing Sheets

SYSTEMS AND METHODS FOR PREDICTING ANIMAL HEALTH

Animal husbandry relates to the raising of animals for a variety of purposes including agriculture, utility, entertainment, companionship, and environmental conservation among others. In agriculture, animals are raised for meat, fiber (e.g., fur), milk, eggs, and other products. Animals are also raised for utility. For example, horses are raised for the purpose of doing work such as carrying people and supplies or pulling carts, plows, or barges. Animals, such as horses, are also raised for entertainment purposes including racing, polo, and other events. Raising animals for companionship occurs with dogs, cats, and other such animals. In environmental conservation, such as the breeding in zoos and in animal preserves, animal husbandry may extend beyond domestic animals. For example, it is desirable to grow the populations of endangered animals or animals with declining populations. In zoos, animal husbandry may relate to the preservation of current animals in the zoo.

The present invention generally relates to improving animal husbandry, and specifically to the health and production vigor of potential offspring through analysis of animal information.

In animal husbandry, it is advantageous to be able to predict if there will be potential health related issues in the breeding lines of animals that can impact the health of the animal, the reproduction vigor of the animal, or in the case of animals consumed by humans, any potential human food safety issues.

In addition to raising healthy animals, animal husbandry is also associated with improving the use of environmental resources associated with raising animals, food quality, food delivery, and product traceability for recall purposes. Thus, it is advantageous to raise animals that minimally impact the environment, are high quality for their purpose (e.g., agriculture, utility, entertainment, companionship, etc.), and are healthy.

Raising healthy animals is beneficial because if an animal gets sick, it may infect other animals. On large farms, hundreds or even thousands of other animals may get sick which will cause financial hardship to the owner of the farm. Thus, it is beneficial to raise animals that are healthy and not prone to disease. Similarly, if animals are raised for food (e.g., meat, eggs, milk, etc.), it is beneficial to raise animals that are healthy and productive.

Conventional animal husbandry relies on a limited set of data to make breeding decisions to raise healthy animals. For example, the date of birth, color, parentage, etc. for specific animals are common data relied upon in conventional animal husbandry analysis. A limitation of the conventional solutions is the reliance on this limited set of data for one specific animal. Conventional solutions typically do not include more detailed data, and thus, a more detailed analysis is foreclosed, which lessens the accuracy of any prediction.

Furthermore, conventional solutions are also limited because they typically do not include health-related data with other data regarding birth, color, parentage, etc. Even when conventional solutions do include health-related data, the quality of the health data may be questionable. For example, an animal may be deemed to be underweight based on a visual observation without measuring the animal on a scale. In this example, the validity of the health data is based on the ability of the observer to detect whether an animal is underweight based on a visual observation. The observer may not have had a good view of the animal, and even if the observer did have full view of the animal, without quantitative measurement, it is impossible to know for certain whether the observer is correct. The quality of the health data may also be questionable because it may have been entered by someone without the proper training or background to make the assessment. For example, the person making the observation may not be a veterinarian or alternatively, have the proper training or experience to make accurate health data determinations.

Conventional animal husbandry analysis of animal data is limited in its ability to accurately predict animal husbandry events such as life span. This is not only due to the limited set of data available in conventional solutions, but also because conventional analysis does not use advanced analytics on the data.

Conventional animal husbandry solutions also fail to accurately explain animal husbandry events. In other words, conventional animal husbandry solutions are limited in their ability to differentiate certain groups of animals and determine which variables were the most important in differentiating the different groups of animals.

To address the limitations specified above, one embodiment provides animal husbandry analytics to make predictions and provide explanations for animal husbandry events.

SUMMARY

Embodiments of the invention provide a computer implemented method, in a data processing system comprising at least one processor and at least one memory, the at least one memory comprising instructions which are executed by the at least one processor to cause the at least one processor to be specifically configured to execute the operations of the method for an intelligent animal health predictor, the method receiving data for an animal, wherein the data is associated with a first criteria; selecting a first machine learning model to analyze the data, wherein the first machine learning model predicts the animal health based on the first criteria; training the first machine learning model, wherein the training comprises generating and selecting features from the data for the animal; applying the first machine learning model to the data for the animal; and outputting predicted health data for the animal based on the first criteria.

Embodiments can further provide restricting the data to information known to breeders when making a breeding decision.

Embodiments can further provide a method wherein the step of training further comprises comparing the predicted health data with the received data to tune the first machine learning model.

Embodiments can further provide a method comprising wherein the first criteria comprises disease resistance, vigor, life expectancy, yield, fertility, deficiencies, robustness, adaptability, efficiency, or growth rate.

Embodiments can further provide a method comprising applying a second machine learning model to the data, wherein the second machine learning model predicts the animal health based on a second criteria.

Embodiments can further provide a method, further comprising training the second machine learning model by generating and selecting features from the data for the animal.

Embodiments can further provide a method comprising stacking the first and second machine learning models.

Embodiments can further provide a method wherein the first machine learning model comprises XG Boost or neural network.

Embodiments can further provide a method comprising wherein the second machine learning model comprises XG Boost or neural network.

Embodiments can further provide a method to form the data of the animals into a lineage related mapping associated with the first criteria.

In another illustrative embodiment, a computer program product comprising a computer usable or readable medium having a computer readable program is provided. The computer readable program, when executed on a processor, causes the processor to perform various ones of, and combinations of, the operations outlined above with regard to the method illustrative embodiment.

In yet another illustrative embodiment, a system is configured to perform various ones of, and combinations of, the operations outlined above with regard to the method illustrative embodiment.

Additional features and advantages of this disclosure will be made apparent from the following detailed description of illustrative embodiments that proceeds with reference to the accompanying drawings.

BRIEF DESCRIPTION OF THE DRAWINGS

The foregoing and other aspects of embodiments of the present invention are best understood from the following detailed description when read in connection with the accompanying drawings. For the purpose of illustrating the invention, there is shown in the drawings embodiments that are presently preferred, it being understood, however, that embodiments of the invention are not limited to the specific instrumentalities disclosed. Included in the drawings are the following Figures.

DETAILED DESCRIPTION

Figure 1:
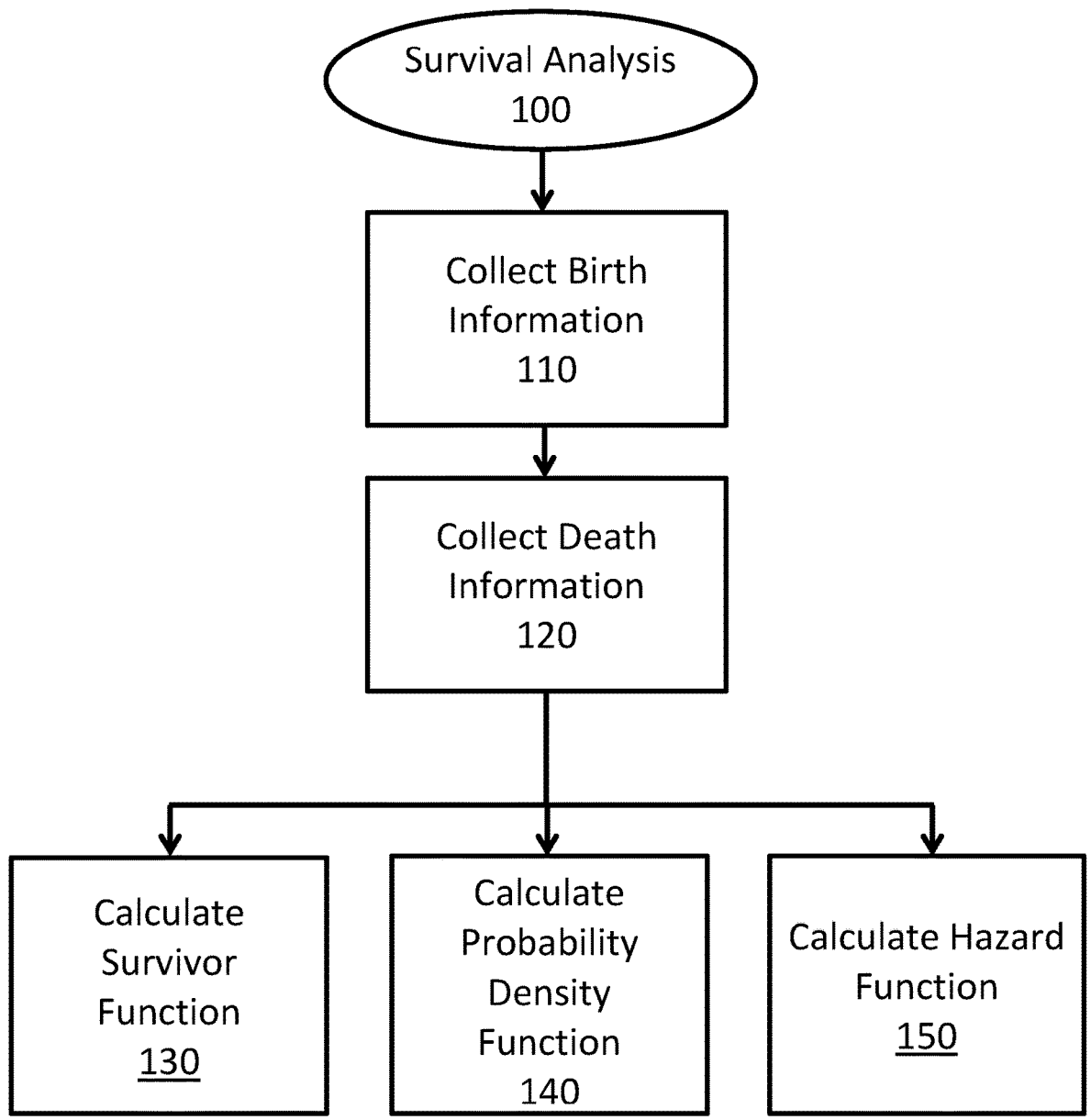
FIG. 1 depicts a flow chart for survival analysis.

The present description and claims may make use of the terms "a," "at least one of," and "one or more of," with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the example provided herein without departing from the spirit and scope of the present invention.

Embodiments of the present invention may be a system, a method, and/or a computer program product. The computer program product may include a computer-readable storage medium (or media) having the computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a head disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network (LAN), a wide area network (WAN) and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Java™, Smalltalk, C++ or the like, and conventional procedural programming languages, such as the "C" programming language or similar programming languages or any other modern programming language, such as Python, or languages specific to machine learning, such as R. The computer readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including LAN or WAN, or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operations steps to be performed on the computer, other programmable apparatus, or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical functions. In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Aspects of the present invention may be implemented on a cognitive system. As an overview, a cognitive system is a specialized computer system, or set of computer systems, configured with hardware and/or software logic (in combination with hardware logic upon which the software executes) to emulate human cognitive functions. These cognitive systems apply human-like characteristics to convey and manipulate ideas which, when combined with the inherent strengths of digital computing, can solve problems with high accuracy and resilience on a large scale. IBM Watson™ is an example of one such cognitive system which can analyze data far faster than human beings and on a much larger scale. In general, such cognitive systems are able to perform the following functions:

1. Ingest and process vast amounts of structured and unstructured data;
2. Generate and evaluate hypotheses;
3. Weigh and evaluate responses that are based only on relevant evidence;
4. Provide situation-specific advice, insights, and guidance;
5. Improve knowledge and learn with each iteration and interaction through machine learning processes;
6. Enable decision making at the point of impact (e.g., what animal lines to breed);
7. Scale in proportion to the task;
8. Deduce potential health of an animal (e.g., disease resistance, longevity);
9. Deduce health and environmental data that is most impactful on animal husbandry factors (e.g., disease resistance, vigor, fertility); and
10. Predict and sense with situational awareness that mimics human cognition based on experiences.

An important factor in animal husbandry is the life expectancy of an animal. Life expectancy can be an indicator for a variety of other important traits in an animal such as health, resistance to disease, vigor, fertility, and tolerance to various environmental factors, among others. One way to determine life expectancy is through a data science technique known as survival analysis.

FIG. 1 illustrates an exemplary flow chart for survival analysis 100. Survival analysis 100 is a prediction of the time until an event. In the field of animal husbandry, the event may be death of the subject animals. In survival analysis, subjects are observed until the event takes place at least with one or more of the subjects. In the case in which not all of the subjects will have experienced the event (e.g., died), the observations are typically referred to as "censored" when the information about their survival time is incomplete. Subjects that do not experience the event after the observation time are said to be "right censored" meaning that the survival time of those subjects is at least the length of the observation time. Censoring is needed in survival analysis because it represents a particular type of missing data. Censoring that is random and non-informative is usually required in order to avoid bias in a survival analysis.

Survival analysis 100, unlike ordinary regression, correctly incorporates information from both censored and uncensored observations in estimating model parameters. There are two dependent variables in survival analysis 100: time to event (e.g., death) and whether or not the event occurred. From these two variables, a survival and hazard function can be determined. The survival function gives, for a specified time, the probability of surviving up to that specified time. The hazard function gives the probability that the event will occur per time unit after a specified time given that the event has not yet occurred prior to the specified time. In other words, the hazard function (or failure rate) is the ratio of the probability density function to the survival function.

The probability density is also useful in survival analysis 100. Probability density represents the probability of the event at any given time. For example, the older an animal gets, the greater chance of dying at a specified age. This is so because the average rate that the event (e.g., death) occurs is calculated as a fraction of the number of units that exist in a specific interval divided by the number of total units at the beginning of the interval.

The first step in survival analysis 100 of animals is to collect birth information 110. In conventional survival analysis, the birth information simply comprises the date of the subject's birth. The subjects are observed over time, and when the subjects die, the death information is collected 120. The present invention contemplates the use of additional birth information as will be discussed below.

Based on the birth and death information, a number of analyses on animal survival can be done, including the survivor function 130, probability density function 140, and the hazard function 150. In animal husbandry, these functions are useful to predict the actual life expectancy of an animal.

The survivor function 130 predicts the probability of the animal surviving to a particular point in time. For example, survivor function 130 for a horse may predict a 90% chance that the horse will live at least 10 years.

In the above example, the probability density 140 can be used to represent the probability of death of the horse at any given time. At two years old, the horse, in the above example, may have a probability of death of only 2%.

Continuing with this example, the hazard function 150 provides the probability that the horse will die after a specified time. For instance, after age 25, there may be a 85% probability that the horse will die in the following year.

Conventional survival analysis gives, for example, a projection or estimation of the actual life expectancy of an animal, but it does not provide a prediction of the potential overall health of a given offspring. In conventional survival analysis, the input to the calculations include the birth and death of the animal under test, but health related information from the animals' parents is not considered.

By analyzing a broad spectrum of data about animals instead of only a conventional survival analysis, better insight can be gained into the factors that are of interest in animal husbandry. As a result, better decisions can be made on the appropriate breeding combinations to improve quality and reduce potential problems in subsequent generations.

Figure 2:
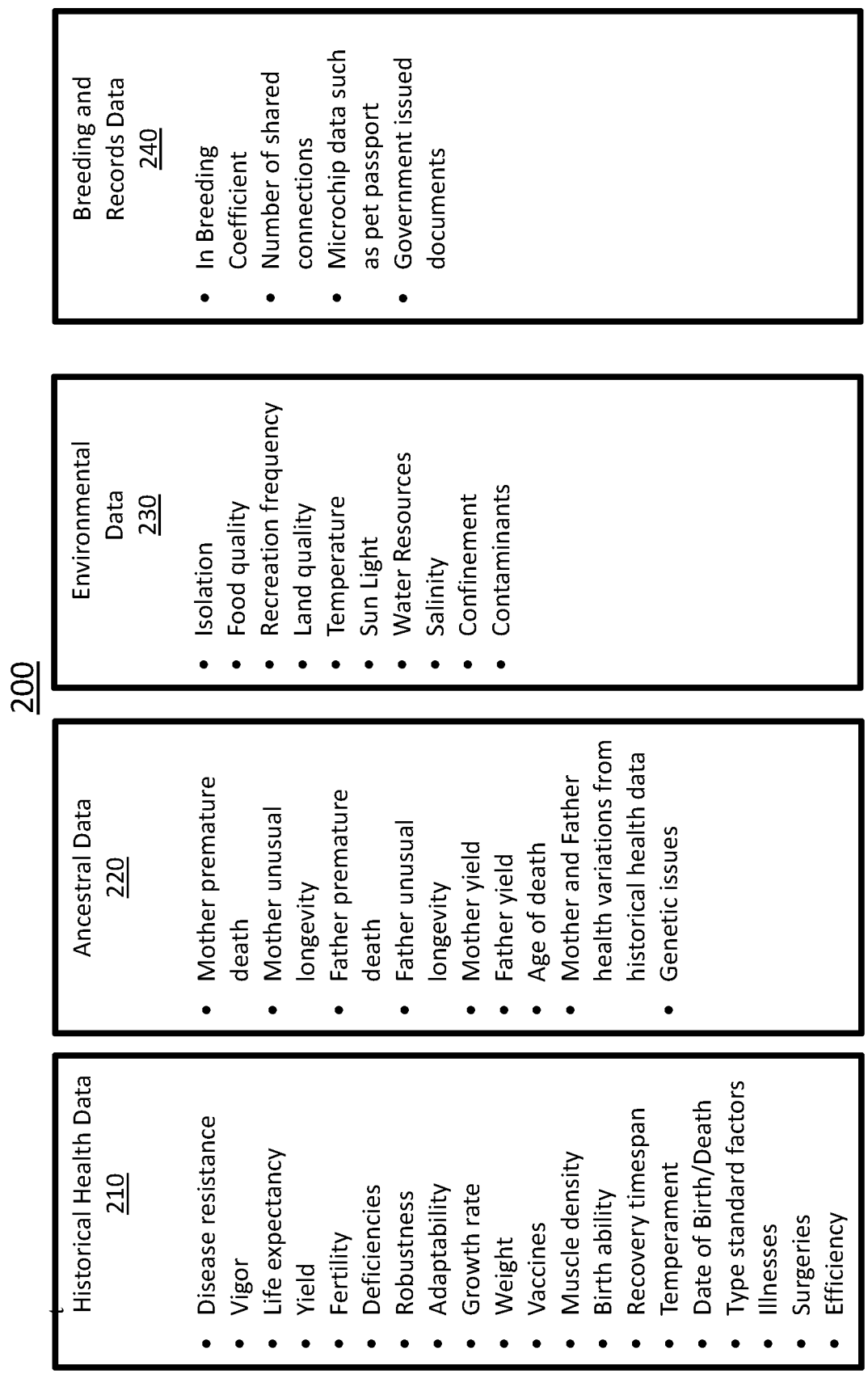
FIG. 2 depicts data.

FIG. 2 discloses data and sources of data 200 that may be used in animal husbandry analysis in accordance with embodiments of the invention. Not every piece of data listed in FIG. 2 may be analyzed as there may be fewer variables considered or more. Furthermore, the data for each variable may have a variety of different formats. For example, information on disease resistance may simply be "disease resistant" or "not disease resistant." In contrast, the format for disease resistance may be a relative number such as on a scale of 1 to 10. If data is captured in an unstructured format, then it may be stored in a non-relational database capable of storing and sorting unstructured data. In the instance in which the data exists as structured data, this data may be collected, stored, and sorted a relational or non-relational database.

Data 200 comprises historical health data 210, ancestral data 220, environmental data 230, and breeding and records data 240. Additional categories of data may also be considered. The exemplary factors shown in FIG. 2 are not limiting.

Exemplary historical health data 210 comprises: disease resistance, vigor, life expectancy, yield, fertility, deficiencies, robustness, adaptability, growth rate, weight, vaccines, muscle density, birth ability, recovery timespan, temperament, date of birth, date of death, type standard factors, illnesses, surgeries, and efficiency. Some health data may be determined by subject matter experts qualified in evaluating the animals for various criterion such as disease resistance. For example, animals may be classified by an expert as disease resistant or not disease resistant. In some instances, offspring may be given a quantitative number to be associated with particular criterion such as based on a scale of 1-10.

Disease resistance may refer to the animal's ability to resist getting a disease, and if sick, how fast does the animal recover. An animal being evaluated for this criteria could be assigned a qualitative answer. For example, the animal might simply be labeled "disease resistant." In another embodiment, the animal could be assigned a quantitative number that is associated with disease resistance and indicates the level of disease resistance that the animal pertains.

Vigor may refer to the level of energy in the animal. Animals with a high level of energy are desirable as there are numerous benefits. For example, a cow with low vigor might be too weak to calve unassisted, which may result in the calf spending extra time in the birth canal. A calf that spends extra time in the birth canal might not get up and readily nurse on its own within the first hour. A calf that nurses within the first hour may get the best colostrum into system to help build immunity. Likewise, a cow that is low in vigor may be low on protein, and a deficiency in protein lowers the quality of the colostrum, which negatively affects the immunity of the calf. Vigor can be identified either qualitatively or quantitatively.

Life expectancy may refer to the length of life of the animal. In some instances, life expectancy may refer to the useable life of an animal. For example, a cow raised for milk production may only be useable for that purpose for about six years. Thus, the life expectancy for a dairy cow may be tied to its ability to produce milk. Typically, life expectancy is a quantitative measure, but in some embodiments, it may be a qualitative measurement such as "exceeds standards."

Yield may refer to the product an animal produces, which can include the animal itself. For example, the yield of a chicken may be the number of eggs it can produce per unit time. Yield from sheep may be the amount of wool that is harvested. Yield typically is a quantitative measure, but in some embodiments, it may be a qualitative measurement such as "exceeds standards."

Fertility may refer to an animal's fertility rate. In livestock production systems, poor fertility is a major factor that limits productivity. Fertility can be identified either qualitatively or quantitatively.

Deficiencies may refer to nutritional deficiencies or mineral deficiencies. Such deficiencies may be the result of genetic or environmental factors. The deficiencies may manifest themselves in the decrease in productivity of the animal, whether that productivity be work, food, or other products (e.g., wool). Deficiencies can be identified either qualitatively or quantitatively.

Robustness in animals may refer to the ability to be resilient to stressors and maintain high production. For example, it is desirable to have animals with high productivity over a wide range of climatic and production conditions. Animals that are under stress release cortisol from the adrenal cortices, which has a wide range of effects on metabolism, the immune system, inflammatory processes, and brain function. In animal production, higher cortisol levels have negative effects on growth rate and feed efficiency and increase the fat/lean ratio of carcasses. Robustness can be identified either qualitatively or quantitatively.

Adaptability may refer to the measure of an animal's ability to adjust to changing circumstances, whether those circumstances are environmental, production conditions, or other. Adaptability can be identified either qualitatively or quantitatively.

Growth rate may refer to the rate at which an animal grows to maturity. Growth rate can be identified either qualitatively or quantitatively.

Weight may refer to the ability of an animal to gain weight. Weight also refers to the weight of the animal. The weight may refer to the animal's weight at a particular point in the animal's life such as at birth, at maturity, or at death.

Vaccines may refer to whether or not the animal was vaccinated as well as the particular vaccines the animal received.

Muscle density may refer to the amount of muscle and or muscle growth. The muscle density may be measured in muscle fiber number per square centimeter. Muscle density may differ between muscle groups, so this data may identify the particular muscle of the animal.

Birth ability may refer to the ease at which an animal gives birth. The more difficult the birth, the more likely there can be side effects or increased risk of mortality to the birthing animal and its offspring.

Recovery timespan may refer to an animal's ability to recover from illness and injury.

Temperament may refer to an animal's characteristic or habitual emotional response. Temperament may refer to the demeanor of an animal in a specific situation. For example, the temperament of cattle during handling in chutes may be identified. Temperament may be indicated as a score on a scale ranging from calm to violent.

Date of birth and death may include additional data such as the time of day of the birth/death.

Type standard factors may refer to the presence and/or measurement of particular factors that are standard for the particular breed of animal.

Illness may refer to the quantity of any illnesses for an animal, and it may refer to the severity of any illnesses. This data may also identify the specific illness(es), or it may simply indicate whether or not the animal ever fell ill.

Surgeries may refer to whether the animal had any surgeries, and it may also indicate the specific surgery(ies) that the animal underwent.

Efficiency may refer to an animal's ability to metabolize food. For instance, an animal that needs little food to be productive is an efficient animal. Efficiency can be identified either qualitatively or quantitatively.

Exemplary ancestral data 220 comprises: premature death of either the mother or father, unusual longevity for either the mother or the father, yield from the mother and father, age of death for the mother and father, any variance of historical health data 210 for either the mother or father, and genetic issues.

The most insightful results regarding the potential animal health generally result by obtaining comprehensive ancestral health data on numerous criterion and for each criteria, collecting data over many generations. A resulting matrix consisting of large quantities of data for a variety of animal health criterion enables a richer analysis and potentially better prediction of animal health.

In an embodiment, the collected ancestral data 220 is stored in a database in the form of a lineage related mapping. In an embodiment, the database is configured to store the lineage related mapping of the ancestral health data for an entire population of animals. In an embodiment, a lineage related mapping uniquely identifies each animal so as to be able to correctly form an ancestral line. The identification information may, in an embodiment, include unique identification information such as, but not limited to, a number, name, or alphanumeric sequence. Furthermore, identification information, in an embodiment, includes information relating to parentage and offspring such that the animal can be properly placed in a lineage mapping. For example, identification information for an animal includes information indicating the identity of its parents and the identities of any offspring. An ancestral line comprises both the maternal and paternal ancestral information. Because each previous animal has two parents, the ancestral database can grow exponentially.

Genetic issues may refer to any known gene in an animal. This includes both dominant and recessive genes. In some cases, a test will need to be done on an animal to determine if there are any gene issues with the animal. In other cases, the gene will manifest itself in the animal so that an observer can identify the presence of the gene. Genetic issues may include predisposition to cancer, skeletal disorders, muscle disorders, etc.

Exemplary environmental data 230 comprises: isolation, food quality, recreation frequency, land quality, temperature, sun light, water resources, salinity, confinement, and contaminants.

Isolation may refer to whether or not the animal was kept isolated or voluntarily remained in isolation. It may also refer to the length of time the animal was isolated, the frequency of isolation, and the like.

Food quality may refer to the type of food. For example, whether or not a cow is grass fed. The level of nutrients in the food may also be an indication of the food quality.

Recreation frequency may refer to whether or not an animal is "free range." This data may not only indicate the frequency of recreation but also the amount of time an animal spends in recreation.

Land quality may refer to whether or not the land upon which an animal lives and grazes is polluted, healthy, nutritious, etc. Land quality may also refer to the physical condition of the land such as whether or not the land is stable or loose such that an animal may get injured.

Temperature may refer to any one or all of the average daily temperature, peak high daily temperature, peak low daily temperature, or the like.

Sun light may refer to the animal's exposure to sun light.

Water resources may refer to the ability of the animal to find fresh water. In addition, water resources may refer to the quality of the water available to the animal.

Salinity may refer to the level of salt in the soil and/or water. Salinity problems reduce productivity of the land, and can have both a direct and indirect effect on animals because of the food and water on the land that the animals eat and drink.

Confinement may refer to whether an animal is kept in confinement and how often. It may also indicate the type of confinement.

Contaminants may refer to the level of pollutants or other contaminants in the food, water, and/or air exposed to the animal. It may also refer to contaminants within the animal itself. Contaminants may also refer to the specific contaminants.

Exemplary breeding and records data 240 comprises both breeding data and sources of data. Exemplary breeding data includes the inbreeding coefficient and the number of shared connections to the animal. Sources of data include data retrieved from a microchip and data from any government or recognized registry issued documents.

The inbreeding coefficient measures the percent increase in homozygous gene pairs in an individual animal relative to the average of the population from which the animal came. The inbreeding coefficient can have any value between 0 and 1.0. For example, in cattle, if a bull has an inbreeding coefficient of 0.25, the bull is expected to have 25% more homozygous gene pairs than a non-inbred animal from the same population.

Figure 3:
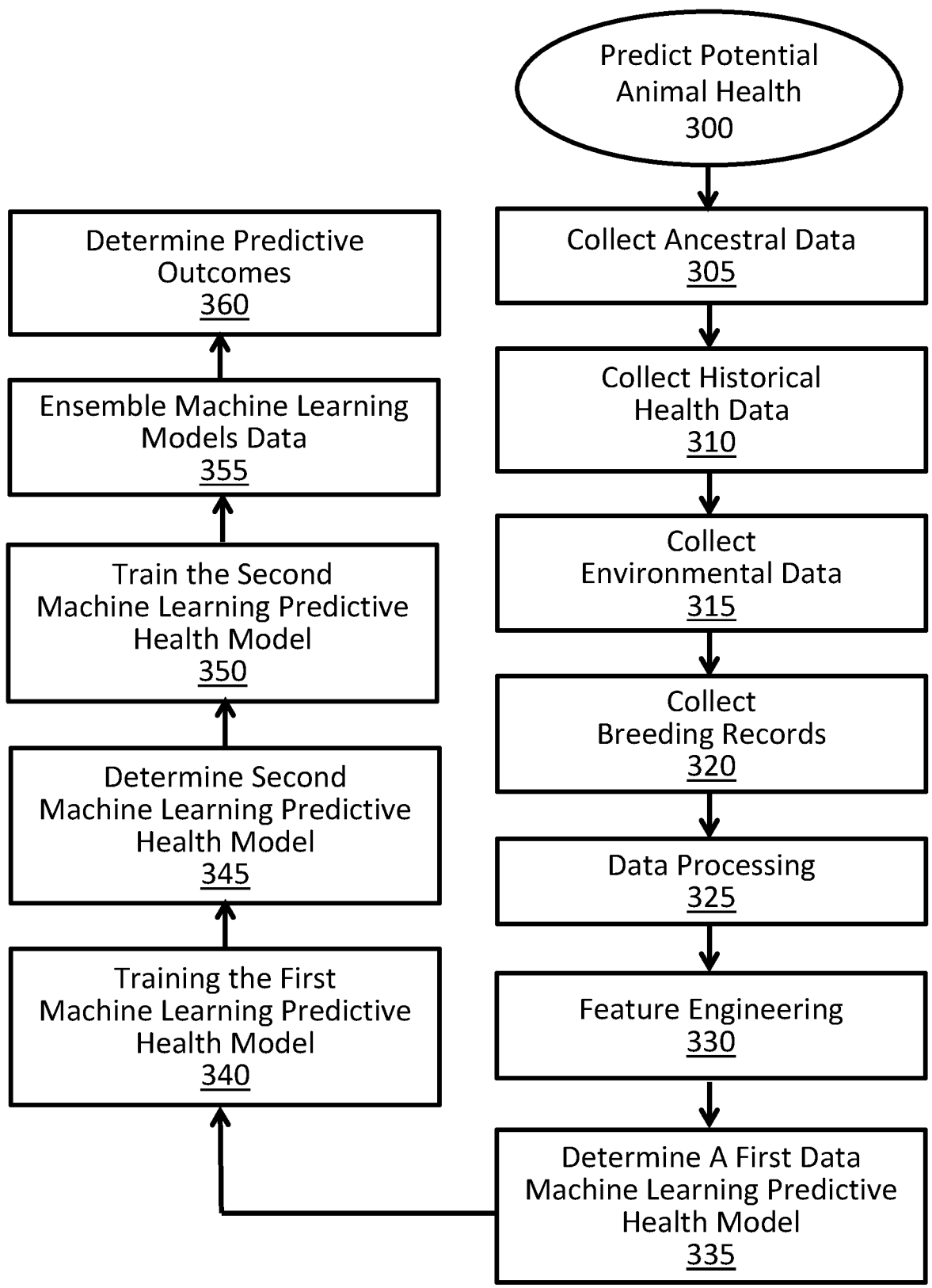
FIG. 3 depicts a flow chart for an animal health prediction method according to embodiments described herein.

FIG. 3 depicts a flow chart for a method to predict potential animal health 300 in accordance with embodiments of the invention. At step 305, ancestral data for a breeding line of animals is collected. At step 310, historical health data is collected for the breeding line of animals. At step 315, environmental data associated with the breeding line of animals is collected. At step 320, breeding records for a breeding line of animals is collected.

At step 325, data processing of the collected data takes place. Data processing comprises the formatting, cleaning, and sampling of the data. First, data is formatted so that it is suitable to work with, such as, for example, inserting the data into a flat file. Next, the data is cleaned by removing or fixing missing data. For example, there may be data instances that are incomplete that need to be removed if they do not contain the information needed. Next, if there is too much data, then the data may optionally be sampled to reduce the run time. Other sampling techniques may be used if the response variable is imbalanced. For example, Synthetic Minority Over-sampling Technique ("SMOTE") can be used during training.

At step 330, feature engineering is performed. This step may comprise scaling, decomposition, and/or aggregation. Scaling is used when the data comprises mixtures of scales and quantities. As the animal data occurs in a wide variety of units and scales, scaling enables data attributes to have the same scale such as between 1-10. Decomposition is useful for the data that is complex and needs to be split. For example, data of date and time may need to be split. Finally, aggregation may be applied to data that can be combined into a single feature.

Next, the data may be split between training, testing, and validation. For example, the split may be 60% of the data is used for training data to fit the predictive model; 30% for testing the predictive model; and 10% for validating the model. In the test set of data, cross-validation can be used. Cross-validation is a technique for evaluating machine learning models by training several machine learning models on subsets of the available input data and evaluating them on the complementary subset of the data. Cross-validation can detect overfitting or failing to generalize a pattern.

At step 335, a first machine learning predictive health model based on a first criteria is determined. In an embodiment, the first machine learning predictive health model will use one or more data collected in steps 305, 310, 315, and 320 to predict the potential health of a given offspring. Optionally, multiple machine learning models can be used that focus on different criteria to create a more robust prediction. A binary or multiclass response can be configured.

Various machine learning algorithms are contemplated by the claimed invention. One such machine learning algorithm is XGBoost. XGBoost is a gradient boosting decision tree algorithm that works well on both basic and more complex recognition problems. This algorithm is also referred to as gradient boosting, multiple additive regression trees, or stochastic gradient boosting. It works by creating a highly accurate classifier by combining many relatively weak and inaccurate classifiers. In other words, new models are added to correct the errors made by existing models. Models are added sequentially until no further improvements can be made.

Another machine learning algorithm that is contemplated by the claimed invention is a neural network. A neural network is a type of machine learning which models itself after the human brain. This creates an artificial neural network that learns by incorporating new data. Neural networks perform deep learning. The basic building block of an artificial neural network is a perceptron which accomplishes simple signal processing. Perceptrons are connected into a large mesh network. Neural networks are taught to do a task by analyzing training data or "learning."

Other machine learning algorithms could also be utilized in embodiments of the claimed invention. The claimed invention is not limited to the XGBoost and neural network machine learning algorithms. For example, Random Forest can be used, which makes predictions by combining the results from many individual decision trees.

After the first machine learning predictive health model is determined, then in step 340, the machine learning model is trained. When training the machine learning model to predict potential health of given offspring, the data that were collected in steps 305, 310, 315, and 320 are used to provide feedback to help the machine learning algorithm "learn." In an embodiment, the data used for training will be restricted to information that would have been known to the breeders at the time of the breeding decision.

The data collected in steps 305, 310, 315, and 320 is used in feature generation. A feature is characteristic of the data. In the training of the machine learning model, feature generation determines a number of features of the data. In some embodiments, the data may contain a large number of features making the learning process time consuming. In an embodiment, to make the data set easier to learn, relevant features are selected to train the machine learning model.

At step 345, in an embodiment, a second machine learning predictive health model can be selected. In this embodiment, the second machine learning predictive health model would be associated with a different aspect of an animal's health than the first machine learning predictive health model. The second machine learning predictive health model may use the same machine learning algorithm as the first machine learning predictive health model. In an embodiment, the second machine learning predictive health model may use a different machine learning algorithm than the first machine learning predictive health model.

At step 350, the second machine learning predictive health model is trained as discussed above.

At step 355 the first and second machine learning predictive health models are combined together in an ensemble method. By ensembling both machine learning models, the predictive accuracy can be boosted. In an embodiment, the first machine learning predictive health model uses XGBoost and the second machine learning predictive health model uses neural networks. Both XGBoost and neural networks have advantages. For example, XGBoost can avoid over-fitting better while neural networks are able to learn more complicated features. Model ensembling leverages the advantages of both models to increase prediction performance. In an embodiment, stacking is used to ensemble the machine learning models together.

At step 360, in an embodiment, the stacked machine learning models determine the potential health of a given offspring. For example, a first machine learning model may be trained on determining if offspring will be disease resistant, and a second machine learning model may be trained on determining if offspring will be robust. The ensemble algorithm can be run against the ancestral data from a male and female animal to predict if the offspring from those two animals would yield disease resistant and robust animals. Other potential insights include the likelihood that the animal may be carrying a specific genetic disorder; the length of hair; whether the animal will be aggressive; yield potential; stamina; and speed.

While FIG. 3 discloses the use of two machine learning algorithms on two different criterion, in other embodiments only a single machine learning algorithm may be used. In still other embodiments, three or more machine learning algorithms may be used. Other embodiments may use different machine learning algorithms on the same criteria.

Figure 4:
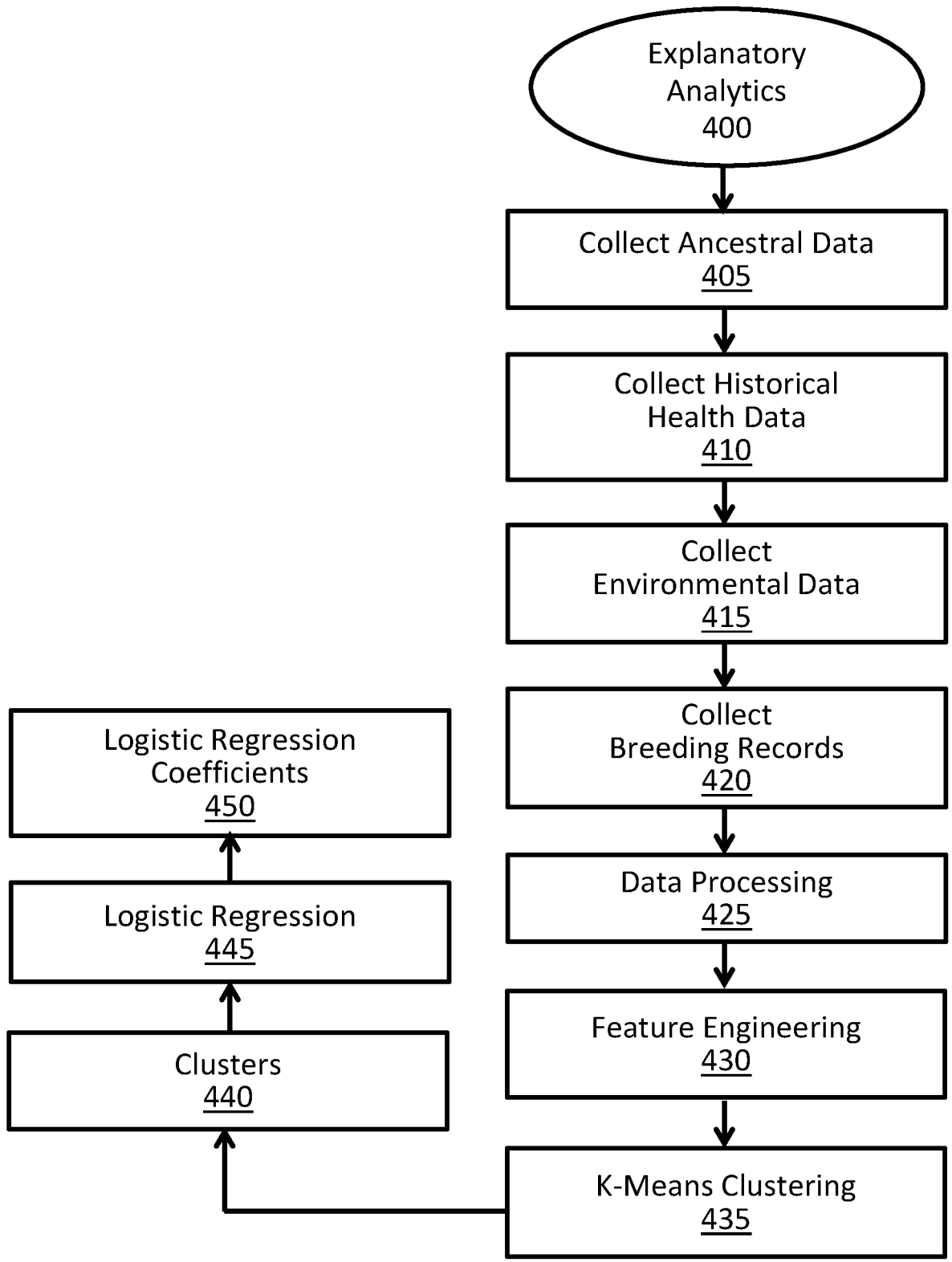
FIG. 4 depicts a flow chart for an animal health analytics method according to embodiments described herein.

FIG. 4 is a method according to embodiments of the invention for analyzing animal data to determine the impact different factors have on an outcome of interest. For example, the factors (e.g., feed, weather, etc.) that most impact yield may be determined by performing explanatory analytics 400 on animal population data.

At step 405, ancestral data for a breeding line of animals is collected. At step 410, historical health data is collected for the breeding line of animals. At step 415, environmental data associated with the breeding line of animals is collected. At step 420, breeding records for a breeding line of animals is collected.

At step 425, data processing of the collected data takes place as set forth in step 325.

At step 430, feature engineering is performed as set forth in step 330. As part of feature engineering for explanatory analytics 400, to handle categorical features such as text values, dummy variables for categorical features need to be created. Dummy variables may be a set of binary (0 or 1) variables that each represent a single class from a categorical feature. For example, assume the data in temperament included: easy, difficult, and dangerous. The corresponding dummy variables might be temperament_easy, temperament_difficult, and temperament_dangerous. If the animal had an easy temperament, then temperament_easy=1, and temperament_difficult=0 and temperament_dangerous=0.

In step 435, k-means clustering is performed on the animal population data. K-means clustering is a type of unsupervised learning that is used to find groups in the data, with the groups represented by the variable k. It is an iterative algorithm that assigns each data point to one of k groups based on the features of the data. Data points are clustered based on feature similarity. K-means clustering results in clusters that are defined by the resulting groups. This is the opposite of a traditional approach in which groups are defined first and then data is attempted to be matched to those groups. K-means clustering may also include a graphic that associates the data with the target number of clusters.

In an embodiment, other clustering algorithms are used. For example, mean-shift clustering, density-based spatial clustering of applications with noise (DBSCAN), Expectation-Maximization (EM) clustering using Gaussian Mixture Models (GMM), and hierarchical clustering.

The result of step 435 are data clusters 440. The data clusters 440 may reveal groups of animals that are candidates for breeding. Other clusters may reveal certain health concerns or environmental problems.

In step 445, a further analysis can be performed on the data clusters 440 with a logistic regression run within each cluster. Logistic regression is a statistical model that models a binary dependent variable with two possible values such as healthy/not-healthy. The probability that an animal is healthy is the log-odds (the logarithm of the odds) of one or more independent variables (e.g., disease-resistance and adaptability). The independent variables can be binary or continuous (any real value).

The logistic regression outputs coefficients 450. These coefficients 450 define the impact different factors have, within a group, on various outcomes. For example, the impact that low salinity water and high quality feed has on growth rate may be determined. Other insights may include the number of C-sections in a cluster; is the animal's mortality higher/lower than the cluster average; is the cluster less healthy; birth defects; and anomaly detection based on the most important logistic regression predictors with a score of greater than 2 Interquartile ranges (IQR) from the group median. The data may comprise weighted data. The weights are determined by the logistic regression.

Figure 5:
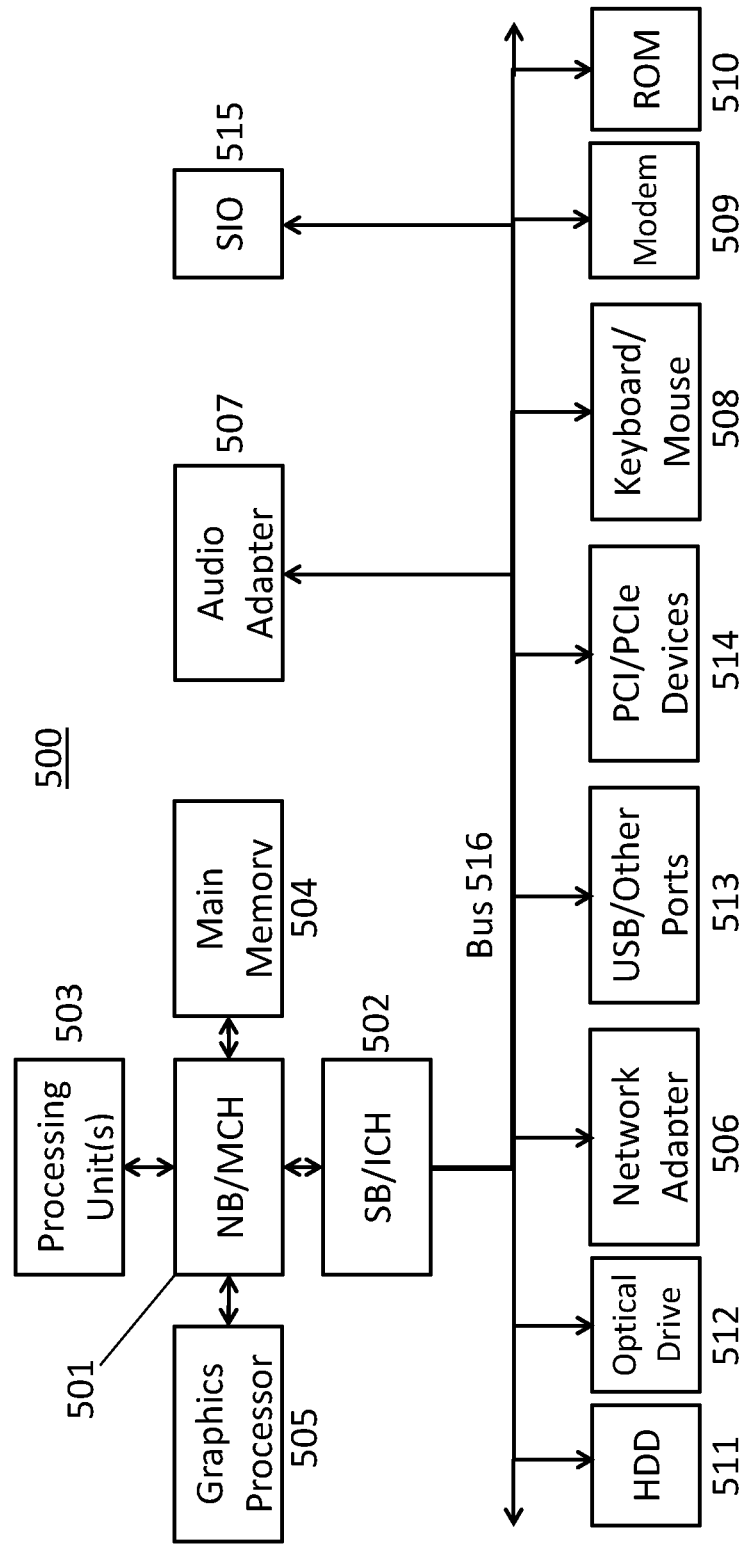
FIG. 5 is a block diagram of an example system in which aspects of the illustrative embodiments may be implemented.

FIG. 5 is a block diagram of an example data processing system 500 in which aspects of the illustrative embodiments can be implemented. Data processing system 500 is an example of a computer, such as a server or a client, in which computer usable code or instructions implementing the process for illustrative embodiments of the present invention are located. In one embodiment, FIG. 5 represents a server computing device, such as a server, which implements the network tracking system described herein.

In the depicted example, data processing system 500 can employ a hub architecture including a north bridge and memory controller hub (NB/MCH) 501 and south bridge and input/output (I/O) controller hub (SB/ICH) 502. Processing unit 503, main memory 504, and graphics processor 505 can be connected to the NB/MCH 501. Graphics processor 505 can be connected to the NB/MCH 501 through an accelerated graphics port (AGP).

In the depicted example, the network adapter 506 connects to the SB/ICH 502. The audio adapter 507, keyboard and mouse adapter 508, modem 509, read-only memory (ROM) 510, hard disk drive (HDD) 511, optical drive (CD or DVD) 512, universal serial bus (USB) ports and other communication ports 513, and the PCI/PCIe devices 514 can connect to the SB/ICH 502 through bus system 516. PCI/PCIe devices 514 may include Ethernet adapters, add-in cards, and PC cards for notebook computers. ROM 510 may be, for example, a flash basic input/output system (BIOS). The HDD 511 and optical drive 512 can use an integrated drive electronics (IDE) or serial advanced technology attachment (SATA) interface. The super I/O (SIO) device 515 can be connected to the SB/ICH 502.

An operating system can run on processing unit 503. The operating system can coordinate and provide control of various components within the data processing system 500. As a client, the operating system can be a commercially available operating system. An object-oriented programming system, such as the Java™ programming system, may run in conjunction with the operating system and provide calls to the operating system from the object-oriented programs or applications executing on the data processing system 500. As a server, the data processing system 500 can be an IBM® eServer™ System p® running the Advanced Interactive Executive operating system or the LINUX® operating system. The data processing system 500 can be a symmetric multiprocessor (SMP) system that can include a plurality of processors in the processing unit 503. Alternatively, a single processor system may be employed.

Instructions for the operating system, the object-oriented programming system, and applications or programs are located on storage devices, such as the HDD 511, and are loaded into the main memory 504 for execution by the processing unit 503. The processes disclosed herein can be performed by the processing unit 503 using computer usable program code, which can be located in a memory such as, for example, main memory 504, ROM 510, or in one or more peripheral devices.

A bus system 516 can be comprised of one or more busses. The bus system 516 can be implemented using any type of communication fabric or architecture that can provide for a transfer of data between different components or devices attached to the fabric or architecture. A communication unit such as the modem 509 or network adapter 506 can include one or more devices that can be used to transmit and receive data.

Those of ordinary skill in the art will appreciate that the hardware depicted in FIG. 5 may vary depending on the implementation. Other internal hardware or peripheral devices, such as flash memory, equivalent non-volatile memory, or optical disk drives may be used in addition to or in place of the hardware depicted. Moreover, the data processing system 500 can take the form of any of a number of different data processing systems, including but not limited to, client computing devices, server computing devices, tablet computers, laptop computers, telephone or other communication devices, personal digital assistants, and the like. Essentially, data processing system 500 can be any known or later developed data processing system without architectural limitation.

The system and processes of the figures are not exclusive. Other systems, processes, and menus may be derived in accordance with the principles of embodiments described herein to accomplish the same objectives. It is to be understood that the embodiments and variations shown and described herein are for illustration purposes only. Modifications to the current design may be implemented by those skilled in the art, without departing from the scope of the embodiments. As described herein, the various systems, subsystems, agents, managers, and processes can be implemented using hardware components, software components, and/or combinations thereof. No claim element herein is to be construed under the provisions of 35 U.S.C. 112, sixth paragraph, unless the element is expressly recited using the phrase "means for."

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A computer implemented method, in a data processing system comprising at least one processor and at least one memory, the at least one memory comprising instructions which are executed by the at least one processor to cause the at least one processor to be specifically configured to execute the operations of an intelligent animal health prediction method comprising:
   receiving a first data set associated with a first animal's ancestors, wherein the first data set comprises historical health and environmental data;
   training a first machine learning model using the first data set to correctly predict the first animal's health according to a first criteria, wherein the first data set is restricted to the historical health and environmental data associated with the first animal's ancestors prior to breeding;
   applying the first machine learning model to a second data set comprising historical health and environmental data associated with a breeding pair of animals to determine a predicted health according to the first criteria of a second animal; and
   outputting the predicted health.

2. The computer implemented method of claim 1, wherein the first criteria comprises disease resistance, vigor, life expectancy, yield, fertility, deficiencies, robustness, adaptability, deficiency, efficiency, or growth rate.

3. The computer implemented method of claim 1, further comprising:
   training a second machine learning model to correctly predict the first animal's health according to a second criteria, wherein the data used in training the second machine learning model is restricted to the historical health and environmental data associated with the first animal's ancestors prior to breeding; and
   applying the second machine learning model to the second data set comprising historical health and environmental data associated with the breeding pair of animals to predict health according to the second criteria of the second animal.

4. The computer implemented method of claim 3, further comprising:
   stacking the first and second machine learning models.

5. The computer implemented method of claim 3, wherein the second machine learning model comprises XGBoost or neural network.

6. The computer implemented method of claim 1, wherein the first machine learning model comprises XGBoost or neural network.

7. The computer implemented method of claim 1, wherein the first data set is formed into a lineage related mapping.

8. The computer implemented method of claim 1, further comprising analyzing the first data set to determine a relationship between the historical health and environmental data with the first animal's health according to the first criteria.

9. The computer implemented method of claim 8, further comprising:
   applying a clustering algorithm to the first data set to determine clusters of the first data set;
   applying logistic regression within each of the clusters to determine the relationship between the historical health and environmental data with the first criteria; and
   outputting from the logistic regression a set of coefficients that represent an impact each data within the first data set has on the first animal's health according to the first criteria.

10. The computer implemented method of claim 1, further comprising training by generating and selecting features from the first data set.

11. A computer program product for an intelligent animal health predictor, the computer program product comprising a computer readable storage medium having program instructions embodied therewith, the program instructions executable by a processor to cause the processor to:
- receive a first data set associated with a first animal's ancestors, wherein the first data set comprises historical health and environmental data;
- train a first machine learning model using the first data set to correctly predict the first animal's health according to a first criteria, wherein the first data set is restricted to the historical health and environmental data associated with the first animal's ancestors prior to breeding;
- apply the first machine learning model to a second data set comprising historical health and environmental data associated with a breeding pair of animals to determine a predicted health according to the first criteria of a second animal; and
- output the predicted health.

12. The computer implemented method of claim 11, wherein the first criteria comprises disease resistance, vigor, life expectancy, yield, fertility, deficiencies, robustness, adaptability, deficiency, efficiency, or growth rate.

13. The computer implemented method of claim 11, further comprising:
- train a second machine learning model to correctly predict the first animal's health according to a second criteria, wherein the data used in training the second machine learning model is restricted to the historical health and environmental data associated with the first animal's ancestors prior to breeding; and
- apply the second machine learning model to the second data set comprising historical health and environmental data associated with the breeding pair of animals to predict health according to the second criteria of the second animal.

14. The computer implemented method of claim 13, further comprising:
- stack the first and second machine learning models.

15. The computer implemented method of claim 13, wherein the second machine learning model comprises XGBoost or neural network.

16. The computer implemented method of claim 11, wherein the first machine learning model comprises XGBoost or neural network.

17. The computer implemented method of claim 11, wherein the first data set is formed into a lineage related mapping.

18. The computer implemented method of claim 11, further comprising analyze the first data set to determine a relationship between the historical health and environmental data with the first animal's health according to the first criteria.

19. The computer implemented method of claim 18, further comprising:
- apply a clustering algorithm to the first data set to determine clusters of the first data set;
- apply logistic regression within each of the clusters to determine the relationship between the historical health and environmental data with the first criteria; and
- output from the logistic regression a set of coefficients that represent an impact each data within the first data set has on the first animal's health according to the first criteria.

20. A system comprising:
- a memory;
- a processor in communication with the memory; and
- program instructions executable by the processor via the memory to cause the processor to:
- receive a first data set associated with a first animal's ancestors, wherein the first data set comprises historical health and environmental data;
- train a first machine learning model using the first data set to correctly predict the first animal's health according to a first criteria, wherein the first data set is restricted to the historical health and environmental data associated with the first animal's ancestors prior to breeding;
- apply the first machine learning model to a second data set comprising historical health and environmental data associated with a breeding pair of animals to determine a predicted health according to the first criteria of a second animal; and
- output the predicted health.

* * * * *